United States Patent [19]

Della Valle et al.

[11] Patent Number: 5,618,842
[45] Date of Patent: Apr. 8, 1997

[54] N-ACYL DERIVATIVES OF AMINOALCOHOLS WITH POLYCARBOXYLIC ACIDS ABLE TO MODULATE MAST CELLS IN INFLAMMATORY PROCESSES HAVING NEUROIMMUNOGENIC ORIGIN

[75] Inventors: Francesco Della Valle; Silvana Lorenzi, both of Padua; Gabriele Marcolongo, Carrara San Giorgio, all of Italy

[73] Assignee: Lifegroup S.p.A., Rome, Italy

[21] Appl. No.: 265,460

[22] Filed: Jun. 24, 1994

Related U.S. Application Data

[63] Continuation-in-part of Ser. No. 998,792, Dec. 30, 1992, abandoned.

[30] Foreign Application Priority Data

Dec. 31, 1991 [IT] Italy ................................. MI91A3509

[51] Int. Cl.$^6$ ................................. A61K 31/155
[52] U.S. Cl. ........................... 514/566; 564/197
[58] Field of Search ............... 514/566; 564/197

[56] References Cited

U.S. PATENT DOCUMENTS

| | | | |
|---|---|---|---|
| 4,452,800 | 6/1984 | Sherlock | 546/122 |
| 4,540,626 | 9/1985 | Haas et al. . | |
| 4,880,834 | 11/1989 | Arch | 514/567 |
| 5,312,986 | 5/1994 | Simon et al. | 564/153 |

OTHER PUBLICATIONS

Journal Of Neuropathology And Experimental Neurology, vol. 44, No. 2, Mar. 1985, pp. 196–203 (Brosman et al).
Journal Of The Neurological Sciences, 105 (1991), pp. 135–142 (Bo et al).
Medical Hypotheses, 1992, 37, pp. 40–43, (Barker et al).
Neuroscience, vol. 57, No. 3, (1993), pp. 861–871 (Theoharides et al).
The Lancet, Feb. 4, 1978, pp. 250–251.
Acta Neurol. Scandinav, 50, (1974), pp. 611–618 (Olsson).
Arteriosclerosis And Thrombosis, vol. 12, No. 11, (1992), pp. 1329–1335 (Lee et al).
TiPS, vol. 13, Jul. 1992, pp. 286–291 (Morganti-Kossmann et al).
Arthritis And Rheumatism, vol. 35, No. 3, Mar. 1992, pp. 351–355 (Aloe et al).
Arthritis And Rheumatism, vol. 27, No. 8, Aug. 1984, pp. 841–844 (Wasserman).
The Journal Of Immunology, vol. 135, No. 2, Aug. 1985, pp. 843s–847s (Levine et al).
The Journal Of Immunology, vol. 142, No. 3, Feb. 1989, pp. 927–931 (Matsuda et al).
British Journal Of Dermatology (1989), 121, pp. 681–688 (Giannetti et al).
Arch Dermatol Res, 277 (1985), pp. 352–358 (Schubert et al).
Eye Science, vol. 2, No. 4 (1986), pp. 245–248 (Mochizuki).
Annals New York Academy Of Sciences, vol. 664 (1992), pp. 425–442 (Sharkey).
Chem Abst 88 (13):83492 1977.
Allerg. Immunol., vol. 19, No. 2–4, 1973, pp. 380–387, V. Astrauskas et al, "Die Wirkung von Antiphologistischen und immunosuppressiven . . . " *Abstract*, p. 383, (English Abstract).
J. Allergy Clin. Immunol., vol. 86, No. 4(2), 1990, pp. 677–683, Mican et al, "Arthritis and mast cell activation", *Abstract*, p. 679, right col., para. 4.
Laboratory Investigation, vol. 48, No. 3, 1983, pp. 332–338, Powell et al, "Early changes in experimental allergic neuritis", *Abstract*, p. 332, left col.
Rheum. Dis. Clin. North. AM., vol. 17, No. 2, 1991, pp. 333–342, Gruber, "Immunoglobulin E, mast cells, endogenous antigens, and arthritis", *Abstract*, *Conclusion*, p. 335, para. 3.
AM. Rev. Resp. Dis., vol. 135, No. 6(2), 1987, pp. S5–S8, Bienenstock et al, "Mast cell involvement in various inflammatory processes", *Introduction*, *Abstract*; Table 1*.
ACTA Neurol. Scand., vol. 81, 1990, pp. 31–36, Kruger PG et al, "Mast cells and multiple sclerosis: a light and electron microscopic study of mast cells in multiple sclerosis emplasizing staining procedures", *Abstract*.
J. AM. Chem. Soc., vol. 79, No. 19, 1957, pp. 5577–5578, Kuehl Jr., et al, "The identification of N–(2–hydroxyethyl)palmitamide as a naturally occurring anti–inflammatory agent", *p. 5577, right col, para. 4*.

*Primary Examiner*—Marianne Cintins
*Assistant Examiner*—Keith MacMillan
*Attorney, Agent, or Firm*—Watson Cole Stevens Davis, P.L.L.C.

[57] ABSTRACT

N-acyl derivatives of aminoalcohols with bicarboxylic or tricarboxylic acids able to modulate the degranulation process consequent to the mast cells activation in inflammatory processes caused by supramaximal stimuli of neurogenic and immunogenic origin.

16 Claims, No Drawings

N-ACYL DERIVATIVES OF AMINOALCOHOLS WITH POLYCARBOXYLIC ACIDS ABLE TO MODULATE MAST CELLS IN INFLAMMATORY PROCESSES HAVING NEUROIMMUNOGENIC ORIGIN

RELATED U.S. APPLICATIONS

This application is a continuation-in-part of application Ser. No. 07/998,792, filed on Dec. 30, 1992, now abandoned, which is herein incorporated by reference.

FIELD OF INVENTION

The present invention relates to the use of N-acyl derivatives of aminoalcohols with bicarboxylic or tricarboxylic acids in the therapeutic treatment of pathologies associated with mast cells degranulation, consequent to a neuroimmunogenic and/or immunogenic hyperstimulation.

PRIOR ART DISCLOSURE

It is known that, when the local homeostasis at the level of the individual systems or compartments is disturbed as a consequence of an exogenous or an endogenous noxa, the human organism uses a complex biologic defence system consisting of a debris removal and of reparative remodeling, said system being known as the inflammatory process.

This process involves locally sequential changes finely regulated by vascular homeostasis, massive cellular infiltrations, local release of several specific chemical mediators and a proliferative and reparative response induction, directed to restore the physiological homeostasis in the damaged zone.

This defence and restoration physiological process may assume pathologic features under conditions of chronic persistence of the noxa initial signals, for example in the autoimmune processes or in case of lack of regulation and control of the physiological process development, as it may occur in the processes of reactive hypersensitivity.

In the autoimmune pathologies the persistence of the trigger noxa results very clearly, as it is represented by the autoantigene, which is of course present in the organism and is erroneously identified by the immune system as exogenous noxa to be destroyed. A very important and up to now not very investigated role is played in the physiologic inflammatory processes by a particular cellular population residing in the tissues, known as Mastocytes or mast cells. These cells begin the inflammatory process, after their activation due to specific signals, achieved through the massive release of several mediators being locally active on the vascular bed, the recruitment, the activation and the migration from the vasal to the tissue compartment of the cellular populations involved in the inflammatory and reparative process. In other words mast cells, normally quiescent, can be activated by particular neurogenic and immunogenic stimuli and this activation results in mast cells degranulation, with the release of substances which produce prevailingly cytotoxic effects. Because of this crucial role, the mast cell population is nowadays acknowledged as the effector system of the inflammation.

The mast cell is therefore at the center of complex interactions, which have an ascertained both physiological and pathophysiological meaning among the nervous system, the endocrine system and immune system and which may be summarized as:

a) pro-inflammatory agonism coming from the nervous system through the neuropeptides, in particular the substance P (neurogenic inflammation);

b) pro-inflammatory agonism coming from the immune system through IgE and Interleukin 1 (immunophlogosis);

c) trophic effects of nervous origin (NGF);

d) negative feed back of the control of the endocrine system mediated by the corticosteroid hormones. (J. Olsson, Int. Rev. Citol., 1968,24, P.27–70; Marshall J. S. and Bienenstock J. Springer, Semin. Immunopath. 1990,12, 191–202).

The mast cell represents at the cellular level the link between the nervous system and the immune system, being its activation under physiological and decidedly pathologic conditions, strictly controlled by both the nervous and the immune system.

Under neuroimmunogenic hyperstimulation conditions, which are present and aggravating in many pathologies having a strong inflammatory component, the mast cell realizes through a degranulation process its "aggressive" potential against its target organ, by releasing cytolesive substances.

In order to understand completely its pathophysiological meaning, it is important to note that mast cells are widely present in different systems and organs in which, when stimulated, determine mainly a localized tissue damage, and that, according to their tissue localization, are distinguishable in two different classes.

In fact both connective and mucosal mast cells were identified. These two mast cells population, although possessing different histochemical and biochemical properties, are both characterized by the ability to synthetize a great variety of cytokines, as well as conventional mediators such as histamine, serotonin, lipidic products, as for example arachidonic acid and prostaglandins and also polysaccharides, such as the heparins and to preserve them in specific stores, which they are released from, as a consequence of the above mentioned neuroimmunogenic stimulation.

As far as the cytokines are concerned, the presence of the Tumor Necrosis Factor (TNF) in preformed prompt release secretory granules results to be of particular relevance (Gordon et al., 1990, Nature, 346 (6281), 274–276).

Cytolithic and antitumoral properties are attributed to TNF, properties which are generally realized through cytotoxicity processes, but the TNF is also involved in articular inflammation processes, proliferation of dermic fibroblasts, osseous remodeling, stimulanion of the toxicity of eosinophils in parasitogenic infections.

One of the most interesting aspects resides in the synthesis conditions of this cytokine, since, as it was previously affirmed, it is also present under cellular rest conditions in the form of granular storages. Under a neuroimmunogenic type stimulus the mast cells release immediately the preformed TNF and synthetize it ex novo.

TNF is therefore the mast cell mediator, which is immediately released, showing then a kinetics extended in time, unlike other prompt release mediators, such as histamine, and that is important in the so called "late phase reactions" which are the main cause of the tissue damage of pathologies associated with mast cells degranulation.

Close to a considerable interest for the activation mechanisms of mast cells, an analogous attention was not observed in the research of the endogenous route of modulation and control of the mast cell hyperactivity, which may be found under many pathological conditions.

All the complex biological systems are regulated by countered mechanisms of agonism and antagonism.

To the neuromediated or immunomediated sequences of mast cell activity, having an agonist meaning towards degranulation, inhibitory antagonist mechanisms acting through local and/or general circuits must correspond in order to maintain the homeostatic equilibrium.

An endogenous mechanism of systemic control of the mast cells behaviour is in any case known, since the endogenous corticosteroid hormones exhibit an antidegranulating activity, preferential for the degranulation induced by immunologic route (Bergstrand E., Bjornsson A., Lundquist B., Nilsson A. and Brattstand R. Allergy, 39, p. 217–230, 1984). These hormones are in any case endowed with pleiotropic activity at the level of many systemic targets and they cannot be considered specific antagonists of the mast cell activation, but rather they must be considered as a macro-response of defence, in case all the local systems of control are overcome by massive generalized insults.

A local control system, acting through endogenous substances representing a first defensive barrier against the pathologic event is however unknown.

From a therapeutic point of view up to now all the attention has been exclusively concentrated on the mast cell as a target exogenous drugs able to inhibit the histamine release as the first and most important mediator involved in the prompt responses of the activation of the inflsmmatory processes.

It is of the early fifties the quite casual discovery of an antiinflammatory activity in a lipidic excipient, utilized as the vehicle of an antirheumatic drug (Long D. A. and Miles A. A., Lancet, 1950, p.492). The successive research directed to identify the agent able to show this action evidenced its presence both in vegetable materials (peanuts oil, soya seeds), and in animal materials (yolk egg mainly).

Only in the middle fifties Kuehl et al.(Kuehl F. A., Jacob T. A., Ganley O. H., Ormond R. E. and Meisinger M. A. P. J. American Chemical Society, 1957, 79 (19), p 5577/8) were able to isolate this substance and then to define its chemical structure which was confirmed to be of N-palmitoylethanolamine (N-PEA), also in view of the comparisons made with the same product obtained by synthesis. (Ganley O. H., Groesslet O. E. and Robinson H. J., J. Lab. and Clin. Med., 1958, 51(5), p.709–714).

The successive pharmacological characterization indicated that N-PEA was active in many inflammation models (Masek K. and Raskova H., Int. Symp. on "Drugs of animal origin"1966, Ferri Edizioni, p. 166–209) and furthermore it resulted also active in increasing the resistance of the animals against various bacterial toxins, and experimental infections.

For the pharmaceutical development, which was successively carried out by these Czechoslovak researchers, the immunostimulating effect of resistance against the bacterial toxins and the experimental infections was considered more important.

A pharmaceutical formulation was prepared and was available on the Czechoslovak market in tablets, each containing 300 mg of active principle known with the name IMPULSIN, and it had, as the main therapeutic indication, the prevention of infections in the respiratory tract. After few years this product was retired from the market because of the poor interest for the chosen indication.

Along the lines followed by the first studies on the identification of these compounds both in vegetable and in animal tissue, an active biochemical type research continued, which was directed to isolate and characterize particular classes of lipids deriving from the N-acylation of membrane phospholipids. In particular, specific classes of phospholipds resulted to be abundant in vegetables tissue and specifically in soybean and pea (Aneja R., Chadha J. S. and Knaggs J. A., Biochem. Biophys. Res. Comm. 36 (3), p. 401–406, 1969; Dawson R. M. C., Clarke N. and Quarles R. H., Biochem. J. 1969,114 p.265–270).

The identification of these compounds in germinal cellular layers or in particular differentiation and/or degeneration states (Gray G. M., Biochim. Biophys. Acta, 1976, 431, p. 1–8; Somerharju P. and Renkonen P., Biochim. Biophys. Acta, 1979, 573, p.83–89) let hypothyze the existence of a specialized functional role of these compounds, although the hypothesis was initially put forth that these products were the result of the activation of the catabolic routes and therefore were degradation products.

The possibility that these compounds could represent a physiological form of defence, directed to block and/or to minimize the damage induced by hypotoxic stress was more clearly put forward by Epps et al. (Biochem. Biophys. Res. Comm., 1979, 90 (2), p.628–633), who found elevated concentrations of N-acylethanolamine in myocardium areas affected with infarction in the dog after coronatic ligature. It was supposed by these authors that these compounds had a physiologic meaning of defence, just in relation to the antiinflammatory activities of N-PEA previously found, without, however, indicating a possible mechanism and/or a preferential site of action, which could correlate the two experimental observations, namely their accumulation in hypotoxic areas and their antiinflammatory activity.

SUMMARY OF THE INVENTION

The Applicant has now found compounds able to modulate the degranulation process consequent to the mast cells activation in inflammatory processes caused by supramaximal stimuli of neurogenic and immunogenic origin.

These compounds are N-acyl derivatives of aminoalcohols with bicarboxylic or tricarboxylic acids.

The present invention therefore relates to the use of these N-acyl derivatives for the preparation of pharmaceutical compositions for the therapeutic treatment of pathologies sustained by mast cells degranulation, as a consequence of a neurogenic and/or immunogenic hyperstimulation.

DETAILED DESCRIPTION OF THE INVENTION

The characteristics and advantages of the N-acyl derivatives suitable for the treatment of the pathologies associated with mast cell degranulation, according to the present invention, are illustrated hereinbelow. The applicant has in fact found that the compounds having these pharmacological properties both in human beings and animals are amides having the formula (I):

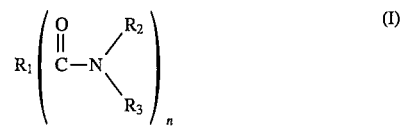

wherein $R_1$ is a divalent or trivalent hydrocarbon radical, optionally substituted with hydroxy or amino groups, n is 2 or 3, $R_2$ is an alcoholic residue selected from a $C_1$–$C_{20}$ linear or branched hydroxyalkyl optionally substituted in the aliphatic chain with one or more aryl groups and a hydroxyaryl optionally substituted with one or more linear or branched alkyl radicals having from 1 to 20 carbon atoms, and $R_3$ is H or equal to $R_2$.

When n=2, the compounds has the formula (II):

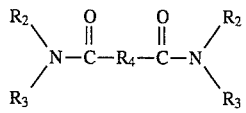

wherein

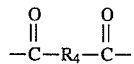

is the acyl radical of a saturated or an unsaturated aliphatic dicarboxylic acid, optionally substituted with a hydroxy or an aminic group, or of an aromatic, heterocyclic or heteroaromatic dicarboxylic acid, and $R_2$ and $R_3$ have the above meaning.

For merely illustrative purposes among the saturated or unsaturated aliphatic dicarboxylic acids there are cited oxalic, fumaric, nonandioic, succinic, trans-2-dodecendioic, glutaric acid, the muconic acids, particularly the trans-trans isomer, and the hydroxy- or amino-substituted homologues of all these acids, and particularly: malic, tartaric, aspartic, glutamic.

Among the aromatic, heterocyclic and heteroaromatic dicarboxylic acids there are cited phthalic acid, cromoglycic acid, 1,4-dihydroxy-2,6-dimethyl-4-(2-nitrophenyl)-3,5-pyridin-dicarboxylic acid, 4,6-dioxo-1-ethyl-10-propyl-4H, 6H,-pyran-[3,2g]-quinolin-2,8-dicarboxylic acid and other biologically acceptable salts.

When n=3, the compounds have the formula (III):

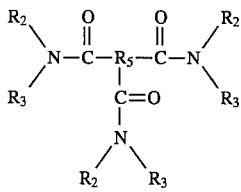

wherein

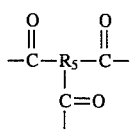

is the acyl radical of a tricarboxylic acid, optionally substituted with hydroxy or amino groups, and preferably of citric acid.

Preferably $R_2$ and $R_3$ are alcoholic residues of ethanolamine, diethanolamine, 2-hydroxypropylamine and di-(2-hydroxypropyl)-amine. In case the alcoholic residue is 2-hydroxypropylamine or di-(2-hydroxy)-propylamine, the corresponding amide is a raceme or an optical isomer.

Examples of the above mentioned compounds are represented by the following formulas:

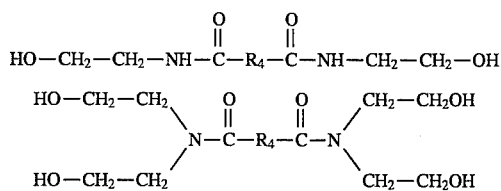

-continued

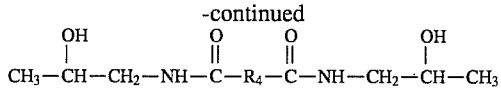

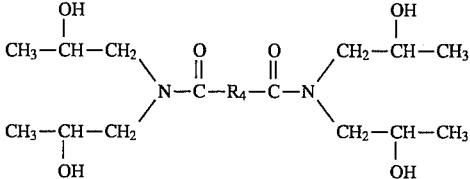

Among the tricarboxylic acids particularly preferred is the citric acid.

Some of the amides according to the present invention are already known in the state of the art, while other ones were prepared by the applicants for the first time; in particular, N,N'-bis(2-hydroxyethyl)-trans-2-dodecendiamide is new.

As already observed, the amides according to the present invention find their applications in all the human and animal pathologies characterized by an inflammatory state of neuroimmunogenic origin, also on autoimmune base, in which it is necessary to carry out a local and selective modulation of the mast cell. In fact said N-acyl derivatives are able to modulate the degranulation consequent to the mast cell activation in inflammatory processes. These substances are suitable to locally perform by exogenous route an antagonist function of these pathological processes acting as local autacoid; this specific pharmacological mechanism has been called ALIA (Autacoid Local Inflammation Antagonism).

The modulation obtained by the controlled inhibition of the maximal degranulation process of the mast cells activated by neuroimmunogenic stimulations, acting by pharmacological route with the substances according to the present invention, results to be an important therapeutical instrument in all the pathologies wherein the mast cell represents the etiopathogenetic effector system.

Taking into account for illustrative purposes the autoimmune field, the most recent prior art provides therapeutically important implications, since the mast cells result to be pathophysiologically involved in many pathologies, as for example the most famous multiple sclerosis and psoriasis.

In multiple sclerosis the pathologically activated mast cells seem to be causally involved in plaques formation in the CNS, in view of the fact that the blood-brain barrier is impaired, permitting the adhesion of the infiltrating granulocytes from the vasal compartment, and that the aggressive cytokine Tumour Necrosis Factor, the final aggressor of the myelinic structures and the ultimate cause of the tissue damages, is released. (Toms R. et al., J. Immunology, 1990, p.169–177; Kruger P. G. et al., Acta Neurol. Scand., 1990, 81, p.31–36).

Also in the case of psoriasis the chronic localized inflammation seems to be directly correlated with vicious mast cells activation. As a matter of fact mast cells degranulation intervenes precociously in the psoriatic lesions development whereas in the chronic situations a considerable increase in mast cells, present in the lesions, is observed (Toyry S. et al., Arch. Dermatol. Res.,1988,280, p.282–285; Toriunowa B. and Jablonka S., Arch. Dermat. Res. 1988,280, p.189–193).

These two pathologies are not the only ones which can be advantageously treated with the N-acyl derivatives according to the present invention, since they are not the only pathologies wherein a mast cell activation is the precocious etiopathogenic effector system of the autoaggressive processes, whose first symptom, locally developing, is an inflammatory process.

In fact the local activation of the mast cells, already residing in the tissues, precedes and conditions the local infiltration of typical cellular populations of inflammation.

The mast cells degranulation seems to determine the vasal permeability and the endothelial adhesion of the leukocytes, which are recruited by the haemat circulation to act on the spot of the pathologic insult. This mechanism has been recently proposed for psoriasis by Matis et al., on the base of precise experimental data Matis et al.,J. Inv. Dermatol. 94,1990, p.492–495).

All the compounds of the above defined class may therefore find a valid therapeutic application, according to their own specific pharmacologic activities, in the following disorders:

dermatologic diseases, such as psoriasis, atopical dermatitis, dermatomyositis, scleroderma, polymyositis, pemphigus, pemphigoid and epidermolysis bullosa;

ophtalmic and mucosal pathologies, such as Sjogren's syndrome, sympathetic ophtalmia, uveitis, uveoretinites and inflammations of the gastrointestinal mucous membranes (Crohn's disease);

articular and connective pathologies, such as rheumatoid arthritis, psoriatic arthritis, lupus erythematosus arthritis, systemic and discoid lupus erythematosus;

chronic inflammatory pathologies, i.e. chronic arthritis, chronic heliomdermatitis, asthma and interstitial pulmonary fibrosis;

degenerative pathologies of PNS and CNS, such as Multiple Sclerosis; neurodegenerative pathologies, not only of autoimmune tyoe, of CNS associated with inflammatory processes, such as Parkinson's disease, senile dementia, bacterial meningitis, HIV infection and traumatic damage, and pathologies of PNS, such as poliradiculopathies of inflammatory type;

peripheral and central nervous system pathologies where inflammatory processes follow a primary injury having ischemic origin, such as peripheral neuropathies due to compressive and traumatic nerve injuries, cerebral stroke and cranial trauma;

cardiological diseases deriving from reperfusion phenomena as a consequence of ischemic insults;

allergic and inflammatory pathologies associated with fibrosis, where the numerical increase and the increase in functional activation of the mast cells is observed, such as allergic conjunctivitis, giant papillary conjunctivitis and dietetic allergies; and cicatrization disorders, such as hypertrophic scars, keloid scars and ocular cicatricial pemphigoid.

Furthermore, with regard to the animal pathology, the local antiinflammatory effect exerted by these new derivatives is useful in the therapy of neurogenic inflammation (i.e. spinal route compression and traumatic nerve lesion in dogs), articular or connective pathologies, such as laminitis in horses (in which the use of corticosteroids is absolutely banned) and arthritis, respiratory disorders, ophtalmic inflammatory pathologies i.e. Keratoconjunctivitis sicca, and finally inflammatory allergic manifestation, including food allergy.

We report hereinbelow for illustrative but not limitative purposes the following examples of the preparation of the amides according to the present invention.

EXAMPLE 1

Preparation of
N,N'-bis-(2-hydroxyethyl)-fumaroyldiamide (1)

1.1 ml fumaroylchloride in 20 ml diethyl ether were added drop by drop to 3.6 ml ethanolamine dissolved in 50 ml methanol and 100 ml diethyl ether in 30 minutes while maintaining the reaction temperature at 0° C.

The reaction was carried out for 1 hour at 0° C. and then completed at room temperature in 4–5 hours.

The obtained precipitate was dissolved in methanol and crystallized in diethyl ether.

The reaction yield was about 70%.

The physical-chemical characteristic of the N,N'-bis-(2-hydroxyethyl)-fumaroyl-diamide product synthetized according to the example 1, are the following:

| | |
|---|---|
| physical state | white crystalline powder |
| raw formula | $C_8H_{14}N_2O_4$ |
| molecular weight | 202.2 |
| elemental analysis | C = 47.52%; H = 6.98%; N = 13.85% |
| | O = 31.65% |
| solubility in organic solvents | hot ethanol <20 mg/ml |
| | DMSO <20 mg/ml |
| solubility in water | <20 mg/ml |
| melting point | 239° C. decomp. |
| TLC | chloroform/methanol/$H_2O$ |
| | (80:20:2) Rf = 0.34 |

EXAMPLE 2

Preparation of
N,N,N',N'-tetra-(2-hydroxyethyl)-fumaroyldiamide (2)

1.53 g fumaroyl chloride (10 mmol) in 20 ml anhydrous diethyl ether were slowly added drop by drop in 30 minutes to a solution of 4.4 g diethanolamine (42 mmol) in 50 ml anhydrous methanol and 100 ml diethyl ether at 0° C. under continuous stirring.

The obtained mixture was maintained at 0° C. for 1 hour under stirring and then at room temperature for 5 hours.

The obtained suspension was filtered, the filtrate was disregarded and the precipitate was crystallized from 20 ml ethanol/isopropanol 1:1, the product was separated by filtration, washed 3 times with 5 ml cool isopropanol and finally dried under high vacuum.

The reaction yield was about 78%.

The physical-chemical characteristics of N,N,N',N'-tetra-(2-hydroxyethyl)-fumaroyl diamide are the following:

| | |
|---|---|
| physical state | white crystalline powder |
| raw formula | $C_{12}H_{22}N_2O_6$ |
| molecular weight | 290.32 |
| elemental analysis | C = 49.65%; H = 7.64%; N = 9.65% |
| | O = 33.07% |
| solubility in organic solvents | >10 mg/ml in DMSO; |
| | >10 mg/ml in hot ethanol. |
| solubility in water | >10 mg/ml |
| melting point | 128–130° C. |
| TLC | chloroform/methanol/$H_2O$/ |
| | (80:25:2:1) Rf = 0.24 |

EXAMPLE 3

Preparation of
N,N'-bis-(2-hydroxyethyl)-nonandiamide (3)

A mixture of 1.88 g azelaic acid (10 mmol) and 1.84 g ethanolamine (30 mmol) was introduced into a flask fitted with a reflux condenser and heated to 160° C. for 6 hours in an oil bath.

The reaction mixture was directly crystallized from 50 ml isopropanol, the crystallized product was separated by filtration, washed 3 times with 10 ml cool isopropanol and finally dried under high vacuum.

The reaction yield was about 78%.

The physical-chemical characteristics of the N,N'-bis-(2-hydroxyethyl)-nonandiamide product are the following:

| | |
|---|---|
| physical state | white crystalline powder |
| raw formula | $C_{13}H_{26}N_2O_4$ |
| molecular weight | 274.37 |
| elemental analysis | C = 56.91%; H = 9.55%; N = 10.21% O = 23.3%. |
| solubility in organic solvents | >10 mg/ml |
| melting point | 132–134° C. |
| TLC | chloroform/methanol/$H_2O$/ $NH_3$ (28%) (80:25:2:1) Rf = 0.48. |

EXAMPLE 4

Preparation of N,N'-bis-(2-hydroxyethyl)-succindiamide (4)

A mixture of 1.18 g succinic acid (10 mmol) and 1.84 g ethanolamine (30 mmol) was introduced into a flask fitted with a reflux condenser and heated to 160° C. for 6 hours in an oil bath.

The reaction mixture was directly crystallized from 20 ml isopropanol, the crystallized product was separated by filtration, washed 3 times with 5 ml cool isopropanol and finally dried under high vacuum.

The reaction yield was about 75%.

The physical-chemical characteristics of the N,N'-bis-(2-hydroxyethyl)-succindiamide are the following:

| | |
|---|---|
| physical state | white crystalline powder |
| raw formula | $C_8H_{16}N_2O_4$ |
| molecular weight | 204.2 |
| elemental analysis | C = 47.06%; H = 7.90%; N = 13.72%; O = 31.34% |
| solubility in organic solvents | >10 mg/ml in DMSO |
| melting point | 153–155° C. |
| TLC | chloroform/methanol/$H_2O$/ $NH_3$ (28%) (80:25:2:1) Rf = 0.24. |

EXAMPLE 5

Preparation of N,N'-bis-(2-hydroxyethyl)-oxalyldiamide (5)

1.46 g diethyloxalate (10 mmol) were slowly added drop by drop in 30 minutes to 1.34 g ethanolamine (22 mmol) at 0° C. under stirring. The obtained mixture was maintained at 0° C. for 1 hour and then at room temperature for 5 hours. The raw product thus obtained was directly crystallized from 50 ml 80% ethanol, the crystallized product was separated by filtration, washed three times with 10 ml cool ethanol and then dried under high vacuum.

The reaction yield was about 91%. The physical-chemical characteristics of the N,N'-bis-(2-hydroxyethyl)-oxalyldiamide are the following:

| | |
|---|---|
| physical state | white crystalline powder |
| raw formula | $C_6H_{12}N_2O_4$ |
| molecular weight | 176.18 |
| elemental analysis | C = 40.9%; H = 6.87%; N = 15.90%; O = 36.33%. |
| solubility in organic solvents | >10 mg/ml in DMSO |
| solubility in water | >10 mg/ml |
| melting point | 168.5–170.5° C. |
| TLC | chloroform/methanol/$H_2O$/ $NH_3$ (28%) (80:25:2:1) Rf = 0.43. |

EXAMPLE 6

Preparation of N,N'-bis-(2-hydroxyethyl)-trans-2-dodecendiamide (6)

A solution of 5.74 g isobutylchloroformiate (42 mmol) in 50 ml THF was slowly added drop by drop in 30 minutes to a mixture containing 4.57 g traumatic acid (20 mmol) and 4.26 g triethylamine (42 mmol) in 150 ml anhydrous THF under stirring at −10° C. The mixture was maintained under stirring at −10° C. for 2 hours and subsequently at 0° C. for 15 hours. 3.5 g ethanolamine were slowly added drop by drop in 30 minutes.

After the reaction was left under stirring for further 6 hours at 0° C., the suspension thus obtained was filtered, the filtrate was disregarded and the precipitate was dried under vacuum. The raw product thus obtained was crystallized from 100 ml water, the product was filtered, washed 3 times with 20 ml water and finally dried under high vacuum.

The reaction yield was about 78%.

The physical-chemical characteristics of the N,N'-bis-(2-idroxyethyl)-dodecendiamide are the following.

| | |
|---|---|
| physical state | white crystalline powder |
| raw formula | $C_{16}H_{30}N_2O_4$ |
| molecular weight | 314.43 |
| elemental analysis | C = 61.12%; H = 9.62%; N = 8.91%; O = 20.35%. |
| solubility in organic solvents | >10 mg/ml in DMSO; >10 mg/ml in ethanol. |
| solubility in water | >10 mg/ml at 95° C. |
| melting point | 134–136° C. |
| TLC | chloroform/methanol/$H_2O$/ $NH_3$ (28%). (80:25:2:1) Rf = 0.57. |

EXAMPLE 7

Preparation of N,N'-bis-(2-hydroxyethyl)-malondiamide (7)

A mixture of 1.32 g dimethylmalonate (10 mmol) and 1.34 g ethanolamine (22 mmol) was introduced into a flask fitted with a reflux condenser and heated to 50° C. for 4 hours in an oil bath. The reaction mixture was directly crystallized from 20 ml isopropanol, the crystallized product was separated by filtration, washed 3 times with 10 ml of cool isopropanol and finally dried under high vacuum.

The reaction yield was about 92%.

The physical-chemical characteristics of the N,N'-bis-(2-hydroxyethyl)-malondiamide are the following:

| | |
|---|---|
| physical state | white crystalline powder |
| raw formula | $C_7H_{14}N_2O_4$ |
| molecular weight | 190.2 |
| elemental analysis | C = 44.21%; H = 7.42%; N = 14.73%; O = 33.65%. |
| solubility in organic solvents | >5 mg/ml in DMSO; >10 mg/ml in ethanol. |
| solubility in water | >10 mg/ml |
| melting point | 127–129° C. |
| TLC | chloroform/methanol/H$_2$O/ NH$_3$ (28%) (80:25:2:1) Rf = 0.38. |

EXAMPLE 8

Preparation of N,N'-bis-(2-hydroxyethyl)-(±)-2-hydroxysuccindiamide (8)

2 g anhydrous sulfonic resin Dowex 50×8 H+ were added to 1.34 g DL malic acid (10 mmol) dissolved in 20 ml anhydrous methanol; the mixture was maintained at 30° C. under stirring for 20 hours. The resin was separated by filtration, the solution was evaporated to dryness and the residue was treated with 1.34 g of ethanolamine for 20 hours at 30° C. The reaction mixture was directly crystallized from 50 ml isopropanol, the crystallized product was separated by filtration, washed 3 times with 10 ml of cool isopropanol and finally dried under high vacuum. The reaction yield was about 73%.

The physical-chemical characteristics of the N,N'-bis-(2-hydroxyethyl)-(±)-2-hydroxysuccinimide are the following:

| | |
|---|---|
| physical state | white crystalline powder |
| raw formula | $C_8H_{16}N_2O_5$ |
| molecular weight | 220.23 |
| elemental analysis | C = 43.63%; H = 7.32%; N = 12.72%; O = 36.33%. |
| solubility in organic solvents | >10 mg/ml in DMSO |
| solubility in water | >10 mg/ml |
| melting point | 124–125° C. |
| TLC | chloroform/methanol/H$_2$O/ NH$_3$ (28%) (88:25:2:1) Rf = 0.17. |

EXAMPLE 9

Preparation of (R,R)-(+)-2,3-dihydroxy-N,N'-bis-(2-hydroxyethyl)-succindiamide (9)

A mixture of 1.78 g dimethyl-L-tartrate (10 mmol) and 1.34 g ethanolamine (22 mmol) was introduced into a flask fitted with a reflux condenser and heated to 40° C. for 20 hours.

The reaction mixture was directly crystallized from 50 ml ethanol, the crystallized product was separated by filtration, washed 3 times with 10 cool ethanol and finally dried under high vacuum.

The reaction yield was about 90%.

The physical-chemical characteristics of the (R,R)-(+)-2,3-dihydroxy-N,N'-bis(2-hydroxyethyl)-succindiamide are the following:

| | |
|---|---|
| physical state | white crystalline powder |
| raw formula | $C_8H_{16}N_2O_6$ |
| molecular weight | 236.25 |
| elemental analysis | C = 40.67%; H = 6.83%; N = 11.86%; O = 40.64%. |
| solubility in organic solvents | >10 mg/ml in DMSO; 10 mg/ml in methanol. |
| solubility in water | >10 mg/ml |
| melting point | 143–145° C. |
| TLC eluent | chloroform/methanol/H$_2$O/ NH$_3$ (28%) (88:25:2:1) Rf = 0.14. |

EXAMPLE 10

Preparation of N,N'-bis-(2-hydroxypropyl)-fumaroyldiamide (10)

1.53 g fumaroylchloride (10 mmol) dissolved in 20 ml anhydrous diethyl ether were slowly added drop by drop to a solution of 3.16 g 3-amino-2-propanol (42 mmol) in 50 ml anhydrous methanol and 100 ml anhydrous diethyl ether in 30 minutes while maintaining the reaction temperature at 0° C.

The reaction was carried out for 1 hour at 0° C., and completed at room temperature in 5 hours and the reaction mixture was finally evaporated to dryness.

The obtained residue was solubilized in 100 ml water and deionized with 30 ml of Bio-Rad AG 501×8 resin and finally lyophilized.

The reaction yield was about 75%.

The physical-chemical characteristics of the N-N'-bis-(2-hydroxypropyl)-fumaroyldiamide are the following:

| | |
|---|---|
| physical state | white amorphous powder |
| raw formula | $C_{10}H_{18}N_2O_4$ |
| molecular weight | 230.25 |
| elemental analysis % | C = 52.17%; H = 7.88%; N = 12.17% O = 27.80% |
| solubility in organic solvents | >10 mg/ml in DMSO |
| solubility in water | >10 mg/ml |
| melting point | / |
| TLC | chloroform/methanol/H$_2$O/ NH$_3$ (28%) (80:25:2:1) Rf = 0.44 |

EXAMPLE 11

Preparation of N,N'-bis-(2-hydroxyethyl)-cromoglycholyldiamide (11)

5.74 g isobutylchloroformiate (42 mmol) in 50 ml DMF were slowly added drop by drop in 30 minutes to 10.25 g disodium cromoglycholate (20 mmol) in 150 ml anhydrous DMF under stirring at −10° C. The mixture was maintained at −10° C. under stirring for 2 hours and then at 0° C. for 15 hours. 3.5 g ethanolamine were then slowly added drop by drop in 30 minutes. After 20 hours under stirring at 0° C. to the obtained suspension 300 ml of a NaCl saturated solution are added and the mixture obtained is extracted 3 times with 100 ml butanol, the extracted fractions are collected and evaporated to dryness. The residue is solubilized in 100 ml water, deionized with 20 ml Bio-Rad AG 501×8 resin and finally lyophilized. The reaction yield was about 71%.

The physical-chemical characteristics of the N,N'-bis-(2-hydroxyethyl)-cromoglycholyldiamide are the following:

| | |
|---|---|
| physical state | white amorphous powder |
| raw formula | $C_{27}H_{26}N_2O_{11}$ |
| molecular weight | 554.52 |
| elemental analysis % | C = 58.48%; H = 4.73%; N = 5.05% |
| | O = 31.74% |
| solubility in organic solvents | >10 mg/ml in DMSO |
| solubility in water | >10 mg/ml |
| melting point | / |
| TLC | chloroform/methanol/H$_2$O/ NH$_3$ (28%) (80:25:2:1) Rf = 0.24 |

EXAMPLE 12

Preparation of N,N'-bis-(2-hydroxyethyl)-aspartyldiamide (12)

2.67 g N-alpha-benzyloxycarbonylaspartic (10 mmol) were solubilized in 20 ml anhydrous methanol, 2 g of an anhydrous sulfonic resin Dowex 50×8 H$^+$ was added to, and the obtained mixture was maintained under stirring at 50° C. for 24 hours. The resin was separated by filtration, the solution was evaporated to dryness and the residue treated with 1.34 ethanolamine at 45° C. for 20 hours.

The reaction mixture was solubilized in 50 ml ethanol/water 1:1 and eluted on a column containing 10 ml of the cationic ion exchange resin Dowex 50×8 generated under H$^+$ form and cooled to 0° C.; the eluate was concentrated to dryness, resolubilized with 50 ml glacial acetic acid and hydrogenated for 20 hours in the presence of palladium black. The solution was evaporated to dryness, the residue resolubilized with 100 ml ethanol/water 1:1 end eluted on a column containing 10 ml of an anionic exchange resin Dowex 1×8 generated under OH$^-$ form and cooled to 0° C. The eluate was concentrated to about 10 ml and finally lyophilized. The reaction yield was about 70%.

The physical-chemical characteristics of the N,N'-bis-(2-hydroxyethyl)-aspartyldiamide are the following.

| | |
|---|---|
| physical state | white amorphous powder |
| raw formula | $C_8H_{17}N_3O_4$ |
| molecular weight | 219.24 |
| elemental analysis % | C = 43.83%; H = 7.82%; N = 19.17% |
| | O = 29.19% |
| solubility in organic solvents | >10 mg/ml in DMSO |
| solubility in water | >10 mg/ml |
| melting point | / |
| TLC | chloroform/methanol/H$_2$O/ NH$_3$ (28%) (80:25:2:1) Rf = 0.05 |

EXAMPLE 13

Preparation of N,N'-bis-(2-hydroxyethyl)-phthaloyldiamide (13)

A mixture of 1.94 g of dimethylphthalate (10 mmol) and 2.44 g ethanolamine (40 mmol) was introduced into a flask fitted with a reflux condenser and heated to 60° C. for 48 hours in an oil bath.

50 ml ethanol were added and the resulting solution was eluted on a column containing 25 ml of a sulfonic resin Dowex 50×8 generated under H$^+$ form, the eluate was evaporated to dryness and the obtained oil was dried under high vacuum.

The reaction yield was about 78%.

The physical-chemical characteristics of N,N'-bis-(2-hydroxyethyl)-phthaloyldiamide produced are the following:

| | |
|---|---|
| physical state | white crystalline powder |
| raw formula | $C_{12}H_{16}N_2O_4$ |
| molecular weight | 252.27 |
| elemental analysis | C = 57.13%; H = 6.39%; N = 11.11% |
| | O = 25.37%. |
| solubility in organic solvents | >10 mg/ml in ethanol |
| solubility in water | >10 mg/ml |
| melting point | / |
| TLC | chloroform/methanol/H$_2$O/ NH$_3$ (28%) (80:25:2:1) Rf = 0.36. |

EXAMPLE 14

Preparation of N,N'-bis-(2-hydroxyethyl)-trans,transmuconoyldiamide (14)

1.42 g trans,trans-muconic acid (10 mmol) were solubilized into 20 ml anhydrous methanol and 2 g of anhydrous sulfonic resin Dowex 50×8 H$^+$ were added to; the mixture was maintained under stirring at 60° C. for 48 hours. The resin was separated by filtration, the solution was evaporated to dryness and the residue treated with 1.34 g ethanolamine at 30° C. for 20 hours. The reaction mixture was directly crystallized from 50 ml isopropanol, the crystallized product was separated by filtration, washed 3 times with 10 ml of cool isopropanol and finally dried under high vacuum.

The reaction yield was about 74%.

The physical-chemical characteristics of N,N'-bis-(2-hydroxyethyl)-trans,trans-muconoyldiamide are the following:

| | |
|---|---|
| physical state | white crystalline powder |
| raw formula | $C_{10}H_{16}N_2O_4$ |
| molecular weight | 228.25 |
| elemental analysis | C = 52.62%; H = 7.07%; N = 12.27%; |
| | O = 28.04%. |
| solubility in organic solvents | >10 mg/ml in DMSO |
| solubility in water | >10 mg/ml |
| melting point | 250° C. |
| TLC | chloroform/methanol/H$_2$O/ NH$_3$ (28%) (88:25:2:1) Rf = 0.65. |

EXAMPLE 15

Preparation of N,N'-bis-(2-hydroxyethyl)-glutaroyldiamide (15)

A mixture of 1.32 g glutaric acid (10 mmol) and 1.84 g ethanolamine (30 mmol) was introduced into a flask fitted with a reflux condenser and heated to 160° C. for 6 hours in an oil bath.

The reaction mixture was directly crystallized from 20 ml isopropanol, the crystallized product was separated by filtration, washed 3 times with 5 ml cool isopropanol and finally dried under high vacuum.

The reaction yield was about 72%.

The physical-chemical characteristics of the N,N'-bis-(2-hydroxyethyl)-glutaroyldiamide are the following:

| | |
|---|---|
| physical state | white crystalline powder |
| raw formula | $C_9H_{18}N_2O_4$ |
| molecular weight | 218.26 |
| elemental analysis | C = 49.53%; H = 8.31%; N = 12.84%; O = 29.32%. |
| solubility in organic solvents | >10 mg/ml in DMSO |
| solubility in water | >10 mg/ml |
| melting point | 119–121° C. |
| TLC | chloroform/methanol/$H_2O$/$NH_3$ (28%) (80:25:2:1) Rf = 0.25. |

BIOLOGICAL ACTIVITY

A—Assumption

Mast cells play an important role in pathological conditions and there is a close connection between their activated states and some specific pathologies.

As previously pointed out, the mast cell is a widely distributed cell in peripheral tissues where it is in anatomical and functional contiguity with nerve endings, particularly with those of peptidergic type.

Under physiological conditions the mast cell is quiescent, but when activated by neurogenic or immunogenic stimuli, it degranulates, releasing substances contained in its granules, some of these substances having pro-inflammatory, chemiotattic and cytotoxyc action, which can promote the so called inflammation phenomenon as well as an autocrine loop of autoactivation.

Due to its anatomo-functional configuration, the mast cell acts as the final mediator of lesive processes at the expense of peripheral tissues. The key role played by the mast cell and by the process of neurogenic inflammation, in which it is involved, have been considered as the causes of the evolution and of the recurrence of clinical manifestations of the above mentioned disorders of autoimmune origin. Such mentioned role of the mast cell is also the cause of not-autoimmune pathologies associated with an inflammatory phenomenon, such as Parkinson's disease, senile dementia, atopic dermatitis or pathologies of PNS, such as poliradiculopathy of inflammatory type, or traumatic and/or toxic pathologies characterized by an endoneural edema of the peripheral nerve.

a) Degenerative pathologies of CNS and of PNS.

In patients affected by Multiple Sclerosis (MS), the presence of mast cells was demonstrated and a key role was attributed to such mast cells in the evolution of clinical symptomatology and in the tissue lesion pathogenesis of this disease, since these cells are not present in not-demyelinated areas or in the corresponding cerebral regions of patients not affected by MS (Y. Olsson, 1974, Acta Neurol. Scandinav. 50, 611–618). MS etiology has not yet been completely explained, but this disease appears in genetically predisposed individuals as a reaction to "environmental" causes. The most important clinical feature is the demyelinated plaque formation in the CNS, for which substance P appears to contribute significantly. Substance P in fact contribute to increase the permeability to hematoencephalic barrier, facilitating the inlet of immunocompetent substances and the inflammatory demyelination and gliosis processes: the presence of positive astrocytes due to the presence of the substance P in the plaques implies a precise role for the neurotransmitter, not only at the onset of the plaques, but also during the whole disease course (R. Barker and A. Larner, 1992, Medical Hypothesis, 37: 40–43).

An experimental model of MS (Experimental Allergic Encephalomyelitis EAE) confirmed that an increase of degranulated mast cells is observed in the regions reached by the inflammatory process (Bo et al., 1991, Journal of Neurological Sciences, 105: 135–142), and that there is the direct participation of these cells in phenomena of myelinic attack, connected with cerebral demyelinating processes. Furthermore some substances, which are able to increase the activation of mast cells, make the symptomatology worse (Theoharides T. C. et al., Neuroscience, 57, 3, 861–871, 1993). The same mechanism can be referred to as regard the pathologies of CNS, which present a neurodegenerative component, not only of autoimmune kind, with the deposition of atheromasic plaques (M. Lee et al., Arteriosclerosis and Thrombosis, 1982, 12: 1329–1335). These disorders have always an inflammatory component mediated by cytokines, which, as already said, are released by mast cells, as for example in the case of senile dementia, bacterial meningitis, HIV infection and mechanical damage (M. C. Morganti-Kossmann et al., TIPS, 13: 2, 86–291, 1992).

Similarly to what happens in CNS, some experimental models of inflammatory demyelinating pathologies of PNS (experimental allergic neuritis) confirmed that an increase of the degranulated mast cells number precedes the appearance of the clear neurologic symptomatology (C. J. Brosman et al., Journal of Neuropathology and Experimental Neurology, 1985, 44, 2: 196–203).

b) Articular pathologies.

Rheumatoid Arthritis (RA) is a multisystemic autoimmune pathology involving the destruction of articular cartilage, tissue erosion and persistent inflammatory synovitis. Synovia is a connective tissue, densely vascularized and innervated by nervous peptidergic fibers, mainly substance P, SP and Calcitonin Gene Relative Peptide (CGRP), whose levels increase duping the inflammatory phase in patients affected by chronic arthritis, included RA. This means that there is a causal correlation between the release of substance P and the inflammation associated with arthritis, probably mediated by the increase in the release of substances acting on vasal permeability. Furthermore, an increase in the substance P levels corresponds to an increase of degranulated mast cells number, and subsequently of the levels of cytokines, such as IL-2 and TNF, as well as of NGF (Aloe et al., Arthritis and Rheumatism, 1992, 35, 3: 351–355).

This result, on the role played by the mast cell in the rise and in the entity of the inflammatory phenomenon at the articular level, has been further confirmed in some experimental models, in which in fact the damage is less intense in animals lacking in mast cells, as well as there is a causal and temporal correlation between mast cell degranulation and the appearance of the damage itself (Wassermann, 1984, Arthritis and Rheumatism, 27, 8: 841–844).

c) Dermal pathologies.

In these diseases the neuropeptides contained at the level of the sensorial cutaneous (SP and VIP) and autonomic (VIP) endings can be locally released by means of antidromic mechanism, inducing mast cell hyperactivation and mediators release (Matsuda H. et al., The Journal of Immunology, 1989, 1412: 927–931). This activation system is involved in the dermal pathologies of inflammatory kind of autoimmune origin, such as psoriasis, or not autoimmune origin, such as atopical dermatitis (Giannetti and Girolomoni, British Journal of dermatology, 1989, 121: 681–688). In psoriasis, in particular, mast cells degranulation was correlated to "recurrence" phenomena (C. Schubert, E. Christophers, Arch. Derm. Res., 1985, 277: 352–358).

d) Ophtalmic and mucosal pathologies.

The same mechanism, ascribable to neurogenic stimuli induced by substance P, are also directly or undirectly involved in ophtalmic autoimmune pathologies such as the uveitis (Mochizuki M., Eye Science, 1986, 2, 4: 245–248), but the involvement of the mast cell is well known even in pathologies of this kind without an autoimmune origin. It was demonstrated that similar involvements take place in inflammatory type gastrointestinal pathologies (K. A. Sharkey, Annals of the New York Academy of Sciences, 1992, vol. 664; 425–441).

PART B—Experimental part i) Biologic activity against mast cells degranulation induced by neurogenic stimuli (Substance P)

In order to verify the specificity of N-acyl derivatives according to the present invention to act as local autacoids when administered by exogenous route under conditions of degranulation induced by mast cells physiological stimuli, the following biological tests were carried out both in vivo and in vitro as described hereinbelow.

In vivo biologic tests: topical and general application 2 weeks old Sprague Dawley rats, provided by Charles River from Calco, were locally treated by intradermal injection on the auricular pinna with the compounds in question at the dose of 0.5 mg/kg, in a buffered aqueous solution at physiological pH.

After 10 minutes a local administration of the substance P (1 μl, $10^{-6}$M), able to induce a mast cells degranulation response, was carried out still by intradermal route.

After 20' from the subtance P administration, the animals were sacrificed and the relative tissue samples (pinna) were taken, for an analysis of the morphological aspect of the mast cells residing in the connective tissues after fixation and coloration with toluidine blue.

The inhibition degree in mast cells degranulation in the tissues of the animals treated with the compounds under question, and compared with those of animals treated only with the physiological degranulation factor (substance P) was considered as a parameter for the biological activity.

From the morphological analysis of the two conditions it resulted that whereas substance P induced a degranulation in the majority of mast cells, under pretreatment conditions with the compounds of the present invention a marked inhibition of this phenomenon was observed. In table 1 the obtained results are reported.

TABLE 1

Effects of the amides according to the present invention against the mast cells degranulation after intradermal administration at the dose of 0.5 mg/kg.

| tested substance | % of degranulated cells |
|---|---|
| solvent | 8 |
| substance P | 94 |
| N,N'-bis-(2-hydroxyethyl)-nonandiamide+ + subst. P | 30 |
| N,N'-bis-(2-hydroxyethyl)-fumaroyl-diamide+ + subst. P | 40 |

The pharmacologic activity of the compounds under question was also verified under conditions of a systemic subcutaneous administration. In this case the animals were firstly treated with 20 mg/kg of the substances under question and after 20 minutes were exposed to the degranulation stimulus with the substance P (1 μl, $10^{-6}$M) in the auricular pinna. Then we proceeded as previously described. In Tab.2 the obtained results are reported on an average of 500–800 cells.

TABLE 2

Effects of N-acyl derivatives according to the present invention after subcutaneous administration of 20 mg/kg.

| tested substance | % of degranulated cells |
|---|---|
| solvent | 12 |
| substance P | 92 |
| (3) + Sub. P | 30 |
| (1) + Sub. P | 28 |
| (4) + Sub. P | 32 |
| (2) + Sub. P | 32 |
| (5) + Sub. P | 45.5 |
| (6) + Sub. P | 33.6 |
| (9) + Sub. P | 32 |
| (7) + Sub. P | 35 |
| (8) + Sub. P | 31 |
| (10) + Sub. P | 38 |
| (11) + Sub. P | 28.6 |
| (12) + Sub. P | 30 |
| (13) + Sub. P | 35.5 |
| (14) + Sub. P | 40.2 |
| (15) + Sub. P | 30 |

In vitro biologic test

Peritoneal mast cells of rat were taken according to the standard methodology described by Lagunoff (1975, Tech. Biochem. Biophys. Morphol., 2, pp. 289–305).

The cells were then cultured in MEM which 10% fetal calf serum was added to and then incubated in a Haereus® incubator for 30 minutes. The derivatives under question at the concentration of $10^{-5}$M were added to the incubation medium.

At the end of the incubation the physiological degranulation stimulus represented by the substance P ($10^{-5}$) was added.

The cells were then centrifugated in order to remove the supernatant formed by the incubation medium and placed onto the slide after coloration with toluidine blue, for the analysis of the morphological aspect at the optical microscope.

Also under these conditions the parameter to be considered was the percentage of degranulated cells after stimulation with the Substance P. The obtained results are indicated in Tab. 3

TABLE 3

Effects of amides according to the present invention against mast cells in vitro.

| tested substance | % of cells undergoing degranulation |
|---|---|
| substance P | 96 |
| (3) + subst. P | 30 |
| (1) + subst. P | 35 |
| (4) + subst. P | 35 |
| (2) + subst. P | 30 |

These results demonstrate that the amides according to the present invention are able to modulate the degranulation processes induced by neuroimmunogenic stimuli, when they are administered by both local and general exogenous route, when the degranulation process induced by the Substance P is being carried out.

ii ) Effects of N,N'-bis-(2-hydroxyethyl)-nonandiamide (ex. No.3) on cutaneous acute inflammation induced by Phorbol 12-myristate 13 acetate.

Materials and Methods:

Balb C mice (weight 18–20 g) were housed under standard conditions (21°–23° C. in 12 hrs light-dark cycle with laboratory food and tap water available ad libitum). The cutaneous inflammation was induced by application of Phorbol-12-myristate 13-acetate (PMA) to the ear (2 μg/ear).
Treatment:

N,N'-bis-(2-hydroxyethyl)-nonandiamide was solubilized in a water:ethanol solution (20:80 v/v) in order to obtain the final concentration of 1; 2.5; 5 and 10%. The solution was applied 1 hour before PMA in two different administrations (60 minutes and 30 minutes before PMA).
Results:

It is well known that PMA inflammation results in mast cell degranulation and furthermore PMA inflammation is less intense in mast cell deficient animals than in normal animals.

The data reported in Table 4 show that N,N'-bis-(2-hydroxyethyl)-nonandiamide is capable to reduce PMA inflammation in a dose-dependent manner and this effect is very clear at 8 hrs and lasts for 48 hrs.

TABLE 4

Protective effect of N,N'-bis-(2-hydroxyethyl)-nonandiamide against Phorbol-12-myristate 13 acetate (PMA) induced inflammation.

| tested substance | hrs: | change in ear thickness (inches × 10E4 ± SEM) after different times (hrs) | | | |
|---|---|---|---|---|---|
| | | 8 | 24 | 48 | 72 |
| PMA | | 130 | 130 | 60 | 50 |
| PMA + ex. No. 3, 10% | | 50 | 50 | 30 | 30 |
| PMA + ex. No. 3, 5% | | 50 | 50 | 40 | 60 |
| PMA + ex. No. 3, 2.5% | | 60 | 60 | 40 | 40 |
| PMA + ex. No. 3, 1% | | 90 | 70 | 50 | — | iii) Effects of N,N'-bis-(2-hydroxyethyl)-fumaroyl-diamide (ex. No. 1) on intraarticular carrageenan induced arthritis in adult rat.
Materials and Methods:

Adult Sprague Dawley rats were injected in the ankle joint with 50 μg of 1% carrageenan physiological saline (0.9% NaCl) or with physiological saline alone.

Injection of carrageenan into the ankle synovium induced inflammation characterized by progressive fibroblast proliferation, lymphocyte infiltration and increased synovium weight and furthermore increased Nerve Growth Factor (NGF) content.
Parameter:

Capability of the molecule under evaluation to reduce inflammation measured as ankle synovium weight and the numbers of degranulated mast cells are evaluated, 48 hours after intraarticular inflammation induction.
Treatment:

N,N'-bis-(2-hydroxyethyl)-fumaroyl-diamide was solubilized in saline and injected intraarticularly at the dose of 20 μg/animal 10 minutes before carrageenan injection.
Results:

Carrageenan inflammation causes i) increasing synovial weight, ii) increase of mast cell (MCs) total number and iii) increase of mast cell degranulation.

The data reported in table 5 show that N,N'-bis-(2-hydroxyethyl)-fumaroyl-diamide is capable to reduce inflammation by reducing both the increase of synovial weight and the number of degranulated mast cells.

TABLE 5

Protective effects of N,N'-bis-(2-hydroxyethyl)-fumaroyl-diamide (ex. No. 1) against carrageenan induced inflammation of ankle joint in adult rat.
A: Reduction of synovial weight.
B: Reduction of degranulated mast cell number.

| A Treatment | Synovial weight (mg) | Decreasing synovial weight (%) |
|---|---|---|
| Sham operated (only injection) | 12.80 ± 3.03 | |
| Saline | 17.20 ± 1.64 | |
| Carrageenan | 76.40 ± 11.59 | |
| Carrageenan + ex. No. 1 | 49.00 ± 6.71* | 35.9 |

| B Treatment | MCs total number/mm2 | Degranulated MCs/mm2 | % | % of inhibition |
|---|---|---|---|---|
| Sham operated (only injection) | 6.80 ± 1.10* | 1.80 ± 1.30* | 26.5 | |
| Saline | 6.20 ± 2.05* | 1.80 ± 0.84* | 29.0 | |
| Carrageenan | 17.80 ± 2.17 | 6.60 ± 1.52 | 37.1 | |
| Carrageenan + + ex. No. 1 | 11.20 ± 3.90* | 2.40 ± 1.14* | 21.4 | 42.2 |

* $p < 0.001$ vs. carrageenan group according to "t" student's test. Each value is the mean value of 5 different observations. The % of inhibition is calculated supposing 100% the carrageenan induced degranulation.

iv) Effects of N,N'-bis-(2-hydroxyethyl)-trans-2-dodecendiamide (ex. No. 6) in the prophylactic adjuvant arthritis test in the rat.

Materials and Methods:

Animals (Female Wistar rat: 150–170 g) were randomized according to body weight in 3 groups (5 animals/group), The arthritic syndrome was induced by a subplantar injection of a fine suspension of dead tubercle bacilli in light liquid Paraffin B.P. into the left hind paw.

Test compound administration:

N,N'-bis-(2-hydroxyethyl)-trans-2-dodecendiamide and indomethacin were prepared in 0.5% Carboxymethyl cellulose (CMC) and administered orally respectively at the dose of 50 mg/kg and 1 mg/kg. Both the compounds were administered daily commencing on the day prior to administration of the adjuvant until the fourteenth day of adjuvant administration (i.e. for 16 days).

Parameter:

Referring to the day of adjuvant administration as day 1, the animals were observed on day 17 and day 24 for the development of secondary lesions as the ears and the tail. Lesions and paws were scored for degree of severity from 0 to 5 and the ears and tail from 0 to 2. The volume of both hind paws was measured at 3, 24 and 48 hours after injection of adjuvant.

Results:

Secondary inflammatory lesions started to occur about 11 days after adjuvant injection. The results described in table 6 indicate N,N'-bis-(2-hydroxyethyl)-trans-2-dodecendiamide possess prominent antiarthritic properties, in particular it causes a marked (59%) and statistically significant inhibition of secondary lesion development on day 24. It has to be noted that the experimental model of arthritis is particularly severe as the rheumatoid arthritis in humans.

TABLE 6

Protective effects of N,N'-bis (2-hydroxyethyl)-trans-2-dodecendiamide (ex. No. 6) on secondary lesion development in the adjuvant arthrytis test.

| Oral treatment | Group mean lesion score (±SD) on day | |
|---|---|---|
| | 17 | 24 |
| Vehicle (CMC) | 11.4 ± 5.62 | 12.1 ± 5.13 |
| Ex. No. 6 | 7.6 ± 2.19 | 5.0 ± 3.16** |
| Indomethacin | 4.4 ± 4.16* | 3.0 ± 3.67** |

SD = Standard Deviation.
Significance of difference from the vehicle treatment group using analysis of variance followed by comparison based on student's "t" distribution: *$p < 0.05$; **$p < 0.01$.

The just quoted experimental data point out the following results:

i) the mast cell degranulation becomes a pathological phenomenon consequently to a neuroimmunogenic and/or immunogenic hyperstimulation;

ii) the excessive degranulation and/or increase in mast cells levels, present in the areas where the inflammation/lesion takes place, is causal to the rise and evolution (chronicity and recurrence) of the pathological phenomenon;

iii) such phenomenon, described as a neurogenic inflammation, is connected with many clinical pathologies;

iv) the limitation of the mast cell activation and degranulation results to be effective in the reduction of various symptomatology, and this proves the terapeutical value of this ALIA molecules. As the compounds according to the present invention are able to show their activity when they are both locally and systemically administered, the administration routes encompassed in the pathologies which can be treated according to the present invention are the dermal topical route, the intra- and trans-dermal route, the intraarticular route, the intracerebroventricular route, the corneal topical route, the intra- and retro-bulbar route, the vaginal route, the topical route on the gastric mucous membrane, the intranasal and the inhaling route, as well all the systemic administrations, and among them the oral route and the parenteral (intravenous, subcutaneous and intramuscular) route.

The necessary doses to have therapeutic effectiveness depend on the administration route and on the pathology severity. Furthermore other factors are to be considered connected with the patients' age, body weight and health general conditions. Anyway an acceptable therapeutic range is comprised between 0.1 mg/kg and 50 mg/kg and preferably between 0.5 and 20 mg/kg.

Relevant undesired side effects being unknown, further to the dosage, a therapeutic regimen has to be established based on medical criteria which take into account the acuity or the chronicity characteristics of the pathology.

Typically the therapeutic regimen may have chronicity features in connection with the different pathologies, with from 1 to 2 daily administrations for at least 4 weeks. In the case of specialistic applications as for example the intraarticular, the intracerebroventricular, the retrobulbar one, weekly administration may be foreseen for at least 4 weeks.

Furthermore, as these pathologies are characterized by new acute phases of the neuroimmunogenic symptomathologies, the amides according to the present invention can be advantageously used for a preventive action as well as for a therapeutic one.

Under these hazard conditions these compounds can be administered as dietetic integrating components, both to human beings and to animals.

The compositions containing as active ingredients the derivatives according to the present invention, comprise all the formulation suitable for the above amentioned administrations and the excipients may be those therapeutically or pharmacologically acceptable suitable for the same applications, as well new excipients able to improve the delivery of these compounds to the site of action.

In this connection also new delivery systems may be considered suitable, which can be obtained by bonding these compounds with specific markers of target tissues, which a preferential tropism, useful as specific vehiculation, exists for.

The preferred formulations for topical administration are the buffered solutions, collyria, gels, patches, lyophilized or granulated powders, suspensions, ovules, aerosols and sprays.

The topical administration of the compounds according to the present invention encompasses a dermocosmetic use, in particular for preventing skin diseases. For the oral systemic administration all the formulations result suitable in the form of dry powder such as granulates, tablets, dragees, perles and in the liquid form such as suspensions or oily perles.

The dietetic integrating components are preferably in the form of tablets or oily perles.

For the parenteral administration the preferred formulations are buffered aqueous solutions or oily suspensions also formed by a lyophilized product readily dispersable in the solvent at the moment of the administration.

The following examples of preferred pharmaceutical compositions are reported for illustrative but not limitative purposes.

EXAMPLE 1

Lacquered tablets
Every tablet contains:

| | |
|---|---|
| Ex. No. 6 | 30 mg |
| O.P. lactose | 80 mg |
| O.P. maize starch | 75 mg |
| O.P. talc | 5 mg |
| O.P. magnesium stearate | 2 mg |
| hydroxypropylmethylcellulose | 2 mg |
| O.P. titanium bioxide | 1.2 mg |
| yellow iron oxide (E172) | 0.2 mg |

EXAMPLE 2

Jelly perles
Every perle contains

| | |
|---|---|
| Ex. No. 5 | 100 mg |
| O.P. peanuts oil | 100 mg |
| O.P. jelly | 52 mg |
| O.P glycerin | 16 mg |
| Erythrosin (E127) | 0.1 mg |

EXAMPLE 3

Lyophilized vials
Every lyophilized vial contains

| | |
|---|---|
| Ex. No. 4 | 50 mg |
| O.P. mannite | 57 mg |
| every vial contains: | |
| water for injectable formulations | 2 ml |

EXAMPLE 4

Dermatologic cream
100 g of cream contain:

| | |
|---|---|
| Ex. No. 3 | 50 mg |
| sorbitan monostearate | 500 mg |
| polyoxyethylensorbitan monostearate | 4.5 g |
| ethyl alcohol | 3 g |
| stearic acid | 3 g |
| paraffin oil | 10 g |
| 70% sorbitol | 6 g |
| methylester of p-benzoic acid | 0.2 g |
| propylester of p-benzoic acid | 0.05 g |
| Water | q.s. to 100 g |

EXAMPLE 5

Ophtalmic ointment

| | |
|---|---|
| Ex. No. 1 | 5 g |
| mineral jelly | q.s. to 100 g |

The pharmaceutical compositions containing as the active principle the compounds of the present invention may find a valid therapeutic application both in human beings and animals, in all the pathologies characterized by mast cells hyperstimulation and wherein it is necessary to modulate the degranulation process induced by neuroimmunogenic stimuli.

The application of these compositions results particularly useful in the following pathologies:

dermatologic pathologies, such as psoriasis, atopical dermatitis, dermatomyositis, scleroderma, polymyositis, pemphigus, pemphigoid and epidermolysis bullosa;

ophtalmic and mucosal pathologies, such as Sjogren's syndrome, sympathetic ophtalmia, uveitis and uveoretinites, and inflammations of the gastrointestinal mucous membranes (Crohn's disease);

articular and connective pathologies, such as rheumatoid arthritis, psoriatic arthritis, lupus erythematosus arthritis, systemic and discoid lupus erythematosus;

chronic inflammatory pathologies, i.e. chronic arthritis, chronic heliomdermatitis, asthma and interstitial pulmonary fibrosis;

degenerative pathologies of CNS and PNS, such as multiple sclerosis; neurodegenerative pathologies of CNS which present an inflammatory component, such as Parkinson's disease, senile dementia and dementia of Alzheimer's type, bacterial meningitis and HIV infection, and pathologies of PNS, such as poliradiculopathy of inflammatory type;

peripheral and central nervous system pathologies where inflammatory processes follow a primary injury having ischemic or traumatic origin, such as peripheral neuropathies, cerebral stroke and cranial trauma;

cardiological type disorders deriving from reperfusion phenomena as a consequence of ischemic insults;

allergic and inflammatory pathologies associated with fibrosis, where the numerical increase and the increase in functional activation of the mast cells is observed, such as allergic conjunctivitis, giant papillary conjunctivitis and dietetic allergies; and cicatrization disorders, such as hypertrophic scars, keloid scars and ocular cicatricial pemphigoid.

Furthermore, the administration of the compositions described in the present invention is useful in some particular veterinary pathologies such as neurogenic inflammation (i.e. spinal route compression and traumatic nerve lesion in dogs); articular or connective inflammations, such as laminitis in horses (in which the use of corticosteroids is absolutely banned) and arthritis; respiratory pathologies; ophtalmic inflammatory pathologies i.e. Keratoconjunctivitis sicca; and finally inflammatory allergic manifestation, including food allergy.

We claim:

1. A method for treating mammalian pathologies associated with mast cell degranulation as a consequence of neurogenic and/or immunogenic hyperstimulation, comprising administering a therapeutically effective amount of an amide of the formula (II):

$$\underset{R_3}{\overset{R_2}{\diagdown}}N-\overset{O}{\underset{\|}{C}}-R_4-\overset{O}{\underset{\|}{C}}-N\underset{R_3}{\overset{R_2}{\diagup}} \quad (II)$$

wherein $$-\overset{O}{\underset{\|}{C}}-R_4-\overset{O}{\underset{\|}{C}}-$$

is the acyl radical of:

a saturated or unsaturated, linear or branched, aliphatic dicarboxylic acid, containing from 2 to 14 carbon atoms, optionally substituted with at least a group selected from —OH and —NH$_2$; or an aromatic dicarboxylic acid selected from the group consisting of phthalic, cromoglycholic, 1,4-dihydroxy- 2,6-dimethyl-4-(2-nitrophenyl)-3,5-pyridin-dicarboxylic and 4,6-dioxo-1-ethyl-10-propyl-4H,6H-pyran-[3,2g]-quinolin-2,8-dicarboxylic acid; and where $R_2$ is an alcoholic residue selected from a $C_1$–$C_{20}$ linear or branched hydroxyalkyl, optionally substituted in the aliphatic chain with one or more aryl groups, and a hydroxyaryl optionally substituted with one or more linear or branched alkyl radicals having from 1 to 20 carbon atoms; and $R_3$ is H or equal to $R_2$; said mammalian pathologies belonging to one of the following subclasses:

human dermatologic pathologies selected from the group consisting of psoriasis, atopical dermatitis, dermatomyositis, scleroderma, polymyositis, pemphigus, pemphigoid and epidermolysis bullosa;

human opthalmic and mucosal pathologies selected from the group consisting of Sjogren's syndrome sympathetic opthalmia, uveitis, uveoretinites and inflammation of the gastrointestinal mucous membranes;

human articular and connective pathologies selected from the group consisting of rheumatoid arthritis, psoriatic arthritis, lupus erythematosus arthritis, systemic and discoid lupus erythematosus;

human chronic inflammatory pathologies selected from the group consisting of chronic arthritis, chronic heliomdermatitis, asthma and interstitial pulmonary fibrosis;

human degenerative pathologies of PNS and CNS selected from the group consisting of Multiple Sclerosis, Parkinson's disease, senile dementia, bacterial meningitis, HIV infection and poliradiculopathy of inflammatory type;

human PNS and CNS pathologies having ischemic and traumatic origin selected from the group consisting of peripheral neuropathies, cerebral stroke and cranial trauma;

human cardiological pathologies deriving from reperfusion phenomena as a consequence of ischemic insults;

human allergic pathologies selected from the group consisting of allergic conjunctivitis, giant papillary conjunctivitis and dietetic allergies;

human cicatrizations disorders selected from the group consisting of hypertrophic scars, keloid scars and ocular cicatricial pemphigoid;

animal pathologies selected from the group consisting of spinal route compression, traumatic nerve lesion, laminitis, arthritis, keratoconjunctivitis, respiratory pathologies, inflammatory allergic manifestation and food allergy.

2. The method according to claim 1 wherein the aliphatic dicarboxylic acid is selected from the group consisting of oxalic, fumaric, nonandioic, succinic, trans-2-dodecendioic, glutaric, malonic, muconic, malic, tartaric, aspartic and glutamic acid.

3. The method according to claim 1, wherein $R_1$ and $R_2$ are alcoholic residues of aminoalcohols selected from the group consisting of ethanolamine, diethanolamine, 2-hydroxypropylamine and di-(2-hydroxypropyl)-amine.

4. The method according to claim 1, wherein said dermatologic pathology is psoriasis.

5. The method according to claim 1, wherein said articular and pathology is rheumatoid arthritis.

6. The method according to claim 1, wherein said amides are topically administered in the form of dermocosmetic compositions.

7. The method according to claim 1, wherein said amides are topically administered in the form of pharmaceutical compositions selected from the group consisting of buffered solutions, collyria, gels, patches, lyophylized and granulated powders, suspensions, ovules, aerosols and sprays.

8. The method according to claim 1, wherein said amides are orally administered as pharmaceutical compositions selected from the group consisting of granulates, tablets, dragees, perles, suspensions and oily perles.

9. The method according to claim 1, wherein said amides are orally administered as dietetic integrating components in the form of dragees, tablets of oily perles.

10. The method according to claim 1, wherein said amides are parenterally administered as pharmaceutical compositions in the form of buffered aqueous solutions or oily suspensions.

11. The method according to claim 1, comprising administering daily from once to twice doses ranging from 0.1 to 50 mg/kg for at least 4 weeks.

12. The method according to claim 11, wherein said doses range from 0.5 to 20 mg/kg.

13. The method according to claim 1, wherein said degenerative pathology of CNS is Multiple Sclerosis.

14. A pharmaceutical composition for the treatment of mammalian pathologies associated with mast cell degranulation as a consequence of neurogenic and/or immunogenic hyperstimulation, containing an effective amount of an amide of formula (II)

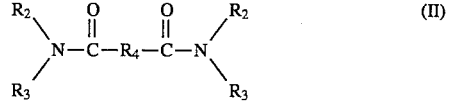

wherein

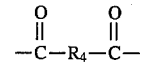

is the acyl radical of: a saturated or unsaturated linear or branched, aliphatic dicarboxylic acid, containing from 2 to 14 carbon atoms, optionally substituted with at least a group selected from —OH and —NH$_2$; or an aromatic dicarboxylic acid selected from the group consisting of phthalic, cromoglycholic, 1,4-dihydroxy-2,6-dimethyl-4-(2-nitrophenyl)-3,5-pyridin-dicarboxylic and 4,6-dioxo-1-ethyl-10-propyl-4H,6H-pyran-[3,2g]-quinolin-2,8-dicarboxylic acid; and wherein $R_2$ is an alcoholic residue selected from a $C_1$–$C_{20}$ linear or branched hydroxyalkyl, optionally substituted in the aliphatic chain with one or more aryl groups, and a hydroxyaryl optionally substituted with one or more linear or branched alkyl radicals having from 1 to 20 carbon atoms; and $R_3$ is H or equal to $R_2$, in association with a pharmaceutical acceptable carrier.

15. The pharmaceutical composition according to claim 14, wherein said aliphatic dicarboxylic acid is selected from the group consisting of oxalic, fumaric, nonandioic, succinic trans-2-dodecendioic, glutaric, malonic, muconic, malic, tartaric, aspartic and glutamic acid.

16. N,N'-bis-(2-hydroxyethyl)-trans-2-dodecendiamide.

* * * * *